United States Patent [19]

Chavez

[11] Patent Number: 4,570,652
[45] Date of Patent: Feb. 18, 1986

[54] TOOTHBRUSH CONTAINER

[76] Inventor: Michael Chavez, 673 E. 137th St. #1B, Bronx, N.Y. 10454

[21] Appl. No.: 519,386

[22] Filed: Aug. 1, 1983

[51] Int. Cl.⁴ .................... A45D 44/18; B65D 83/10
[52] U.S. Cl. ............... 132/84 R; 206/362.2; 132/84 D
[58] Field of Search ........... 132/84 R, 84 A, 84 B, 132/84 C, 84 D, 79 F, 79 R, 79 B, 79 A; 206/209, 361, 362, 362.2, 362.3

[56] References Cited

U.S. PATENT DOCUMENTS

| | | | |
|---|---|---|---|
| 23,038 | 2/1894 | Wagandt | D6/94 |
| 162,978 | 4/1951 | Neumann | D4/3 |
| 193,764 | 10/1962 | Gygie | D4/3 |
| 241,591 | 9/1976 | Fentules | D23/02 |
| 1,713,379 | 5/1929 | Fromwiller | 206/362.2 |
| 2,455,600 | 12/1948 | Molumby et al. | 132/84 R |
| 2,538,337 | 1/1951 | Spears | 206/362.2 |
| 2,599,019 | 6/1952 | Rupert | 132/84 R |
| 2,725,270 | 11/1955 | Upchurch | 206/362.2 |
| 3,007,618 | 1/1959 | Davis et al. | 224/42.45 |
| 3,124,399 | 3/1964 | Seta | 206/362.2 |
| 3,746,162 | 7/1973 | Bridges | 206/361 |
| 4,049,126 | 9/1977 | Halverson | 211/104 |
| 4,214,657 | 7/1980 | Winston | 206/362.1 |
| 4,221,014 | 9/1980 | Davidson | 9/1.1 |
| 4,234,087 | 11/1980 | Pandak | 206/362.2 |

Primary Examiner—Gene Mancene
Assistant Examiner—Carolyn A. Harrison
Attorney, Agent, or Firm—Roger S. Thompson

[57] ABSTRACT

A toothbrush container assembly for use with a toothbrush and for mounting in a wall including a base having a first aperture therein, a slot adjacent said first aperture, an interior reservoir, a second aperture leading from the reservoir to the exterior of the base, the second aperture including a first fastener and means for securing the base to the wall, and a toothbrush container assembly having a cap including a second fastener; a central housing including first and second ends, a third fastener disposed at the first end and adapted to removably engage the second fastener, a fourth fastener disposed at the second end of the housing and adapted to removably engage said first fastener; and engaging hook disposed intermediate the first and second ends and adapted to removably engage the slot; an interior shoulder to support the toothbrush while within the container; a first, perforated, bottom member having a fifth fastener adapted to removably engage the fourth fastener; and a second, imperforate, bottom member having a sixth fastener adapted to removably engage the fourth fastener.

7 Claims, 8 Drawing Figures

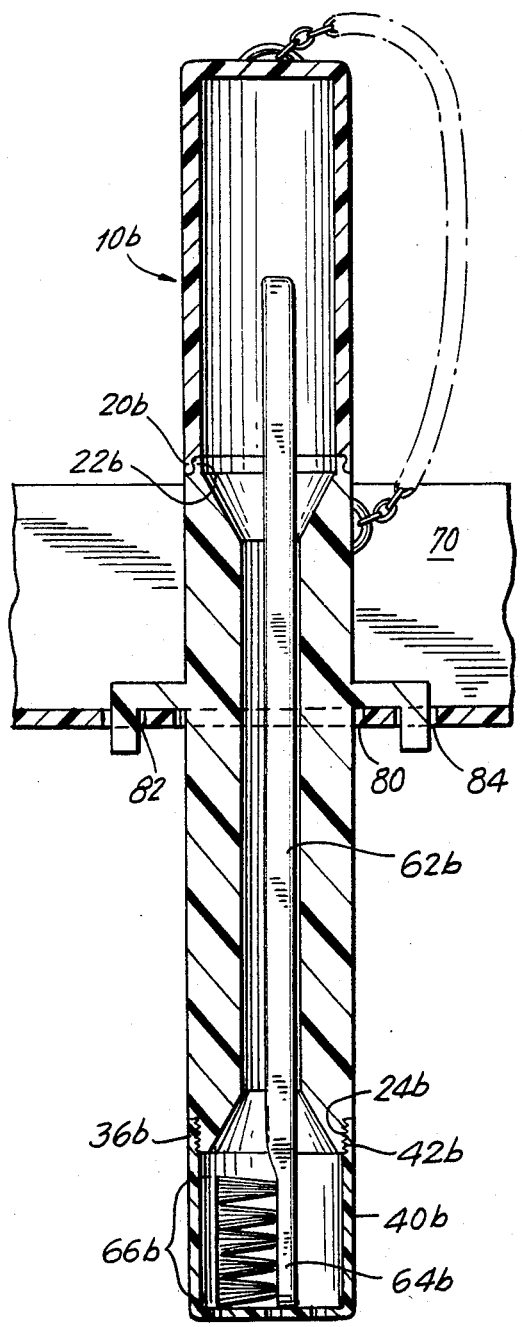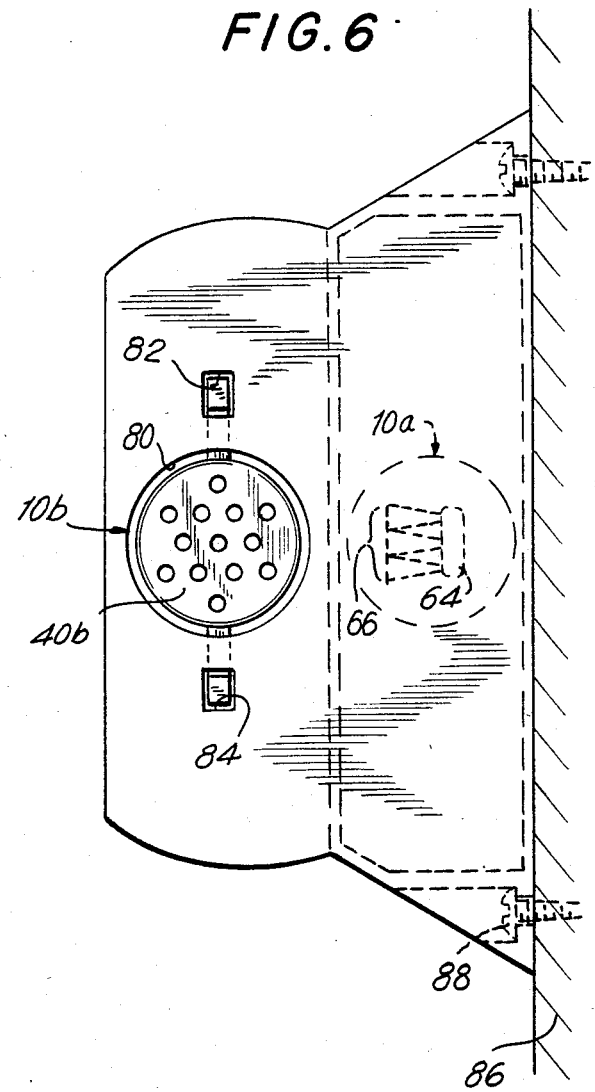

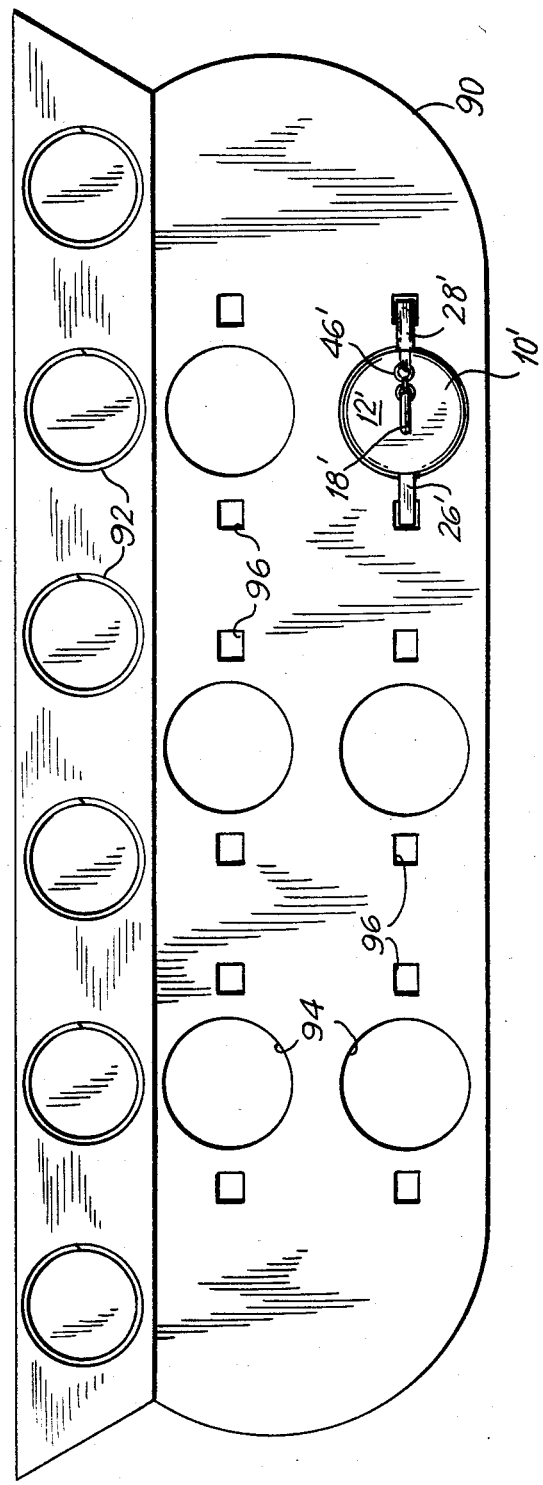

TOOTHBRUSH CONTAINER

This invention relates to the field of toothbrush containers, and, more particularly, to a toothbrush container which may be used to disinfect a toothbrush while it is being stored.

Many containers for transporting toothbrushes are known, and such containers generally comprise simple boxes which do little more than surround the toothbrush, and thereby prevent the toothbrush from soiling anything with which it would otherwise come in contact, for example, while packed in a suitcase. Such known devices have many drawbacks.

Their most serious drawback is that they do not provide any means for disinfecting the bristles of the brush after it has been used. After use, the bristles of the toothbrush may retain a certain amount of dentifrice therein and also, perhaps, food particles, all of which may serve as a breeding ground for bacteria. Even after rinsing the brush, much of the residue of such substances will remain, trapped in the bristles. In fact, if a toothbrush is placed in a closed receptacle immediately after rinsing, the dampness of the bristles containing dentifrice and/or food particles, may render that area more conducive to the growth of unwanted bacteria.

To ameliorate this effect, other prior art toothbrush containers have utilized drying holes in their exteriors, to expose the bristles of the toothbrush to ambient air so that they may dry more quickly. This construction, however, is only useful at certain times, and at other times may be a drawback, e.g. once the bristles are dryed it would be preferred to have the container completely sealed, to prevent contamination.

Additionally, known toothbrush containers are suitable only for traveling, and are not generally suitable for use in the home. In a large family, there may be several toothbrushes in use, one for each member of the family, and it would be advantageous to provide each member of the family with a separate toothbrush container which may be used either at home or while traveling, and which may both protect the toothbrush and provide means for disinfecting the toothbrush. In a large household, this could mean a multiplication of containers, and lead to a confusing clutter in the place in which such containers are stored.

It is an object of the invention to overcome these drawbacks and to provide a toothbrush container which includes means for disinfecting the toothbrush after use.

It is another object of the invention to provide a toothbrush container which is adaptable for use to house a toothbrush while wet to allow it to dry, and also adaptable to house a toothbrush while dry to keep it completely protected from anything with which it may come in contact.

It is a further object to provide a toothbrush container which is adaptable for use in the home as well as suitable for use while traveling.

In accordance with these and other objects of the invention, the inventive toothbrush container, which is intended for use with a base, includes: a housing, having an interior wall and first and second ends; at least one shoulder fixed to the interior wall of the housing; a cap adapted to securely engage the first end of the housing; at least one bottom member adapted to securely engage the second end of the housing; and securing means, mounted on the exterior of the housing for securing the toothbrush container to the base.

The above brief description, as well as further objects, features and advantages of the present invention, will be more fully understood by reference to the following detailed description of a preferred, but nonetheless illustrative embodiment of the present invention, when taken in conjunction with the accompanying drawings wherein:

FIG. 5 is a second cross-sectional view of the embodiment of FIG. 3, taken along the line 5—5 therein;

FIG. 6 is a bottom plan view of the embodiment of FIG. 3; and

FIG. 7 is a top plan view of a secondary embodiment of a portion of the invention.

Figure 1:
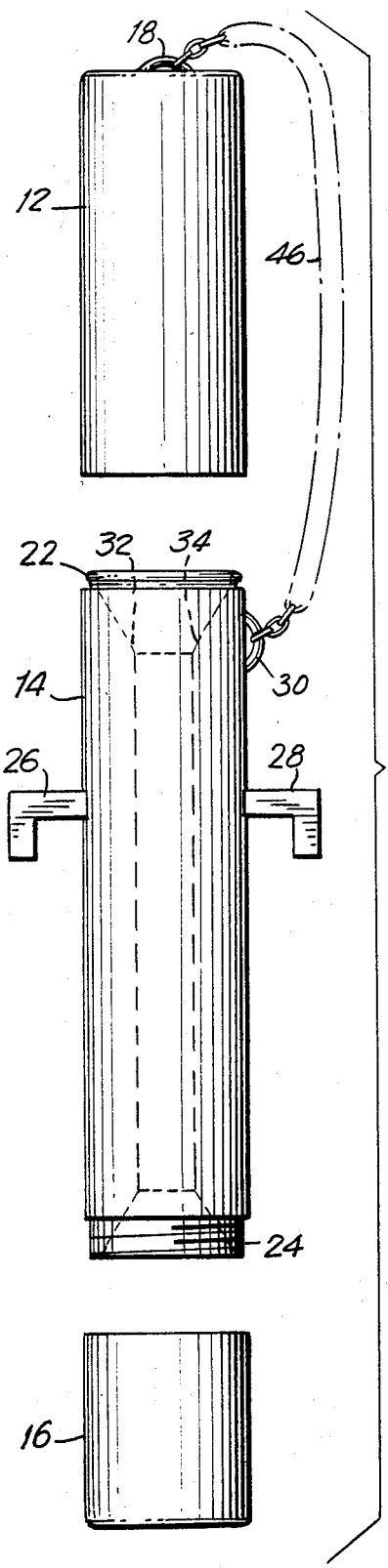
FIG. 1 is an exploded elevational view of a toothbrush container manufactured in accordance with the invention.

The basic design for a toothbrush container manufactured in accordance with the invention is shown in FIG. 1.

Figure 4:
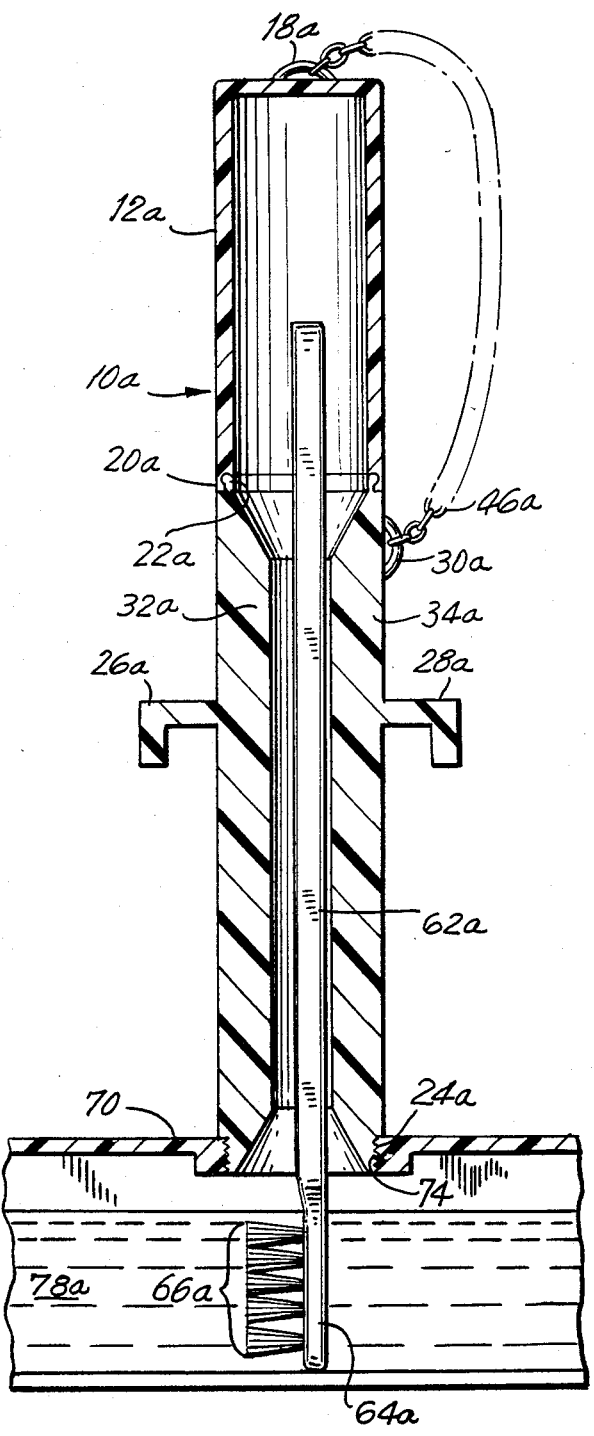
FIG. 4 is a front cross-sectional view of the embodiment of FIG. 3, taken along the line 4—4 therein.

Toothbrush container 10 comprises generally three pieces, a cap 12; a central housing 14 and a first bottom member 16. Cap 12 may include an eyelet 18 disposed on one end thereof, and a first fastener 20, such as a female end of a snap-fit fastener (see, e.g. FIGS. 4 and 5).

Housing 14 includes a second fastener 22 adapted to engage first fastener 20 of cap 12, and which is disposed at a first end of housing 14; a third fastener 24, such as a first set of threads, disposed at the opposite end of housing 14; a pair of hooks 26, 28 disposed intermediate said second and third fasteners 22, 24; a second eyelet 30; and a pair of shoulders 32, 34 disposed in the interior of housing 14.

First bottom member 16 includes a fourth fastener 36, such as a second set of threads (see, e.g. FIG. 5) adapted to engage third set of threads 24; and a solid bottom 38.

Figure 1A:
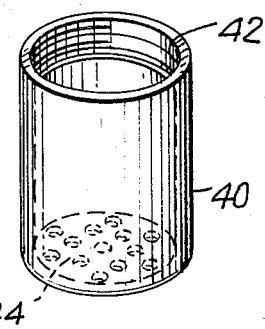
FIG. 1A is a top perspective view of an alternative embodiment of a portion of the container shown in FIG. 1.
Figure 2:
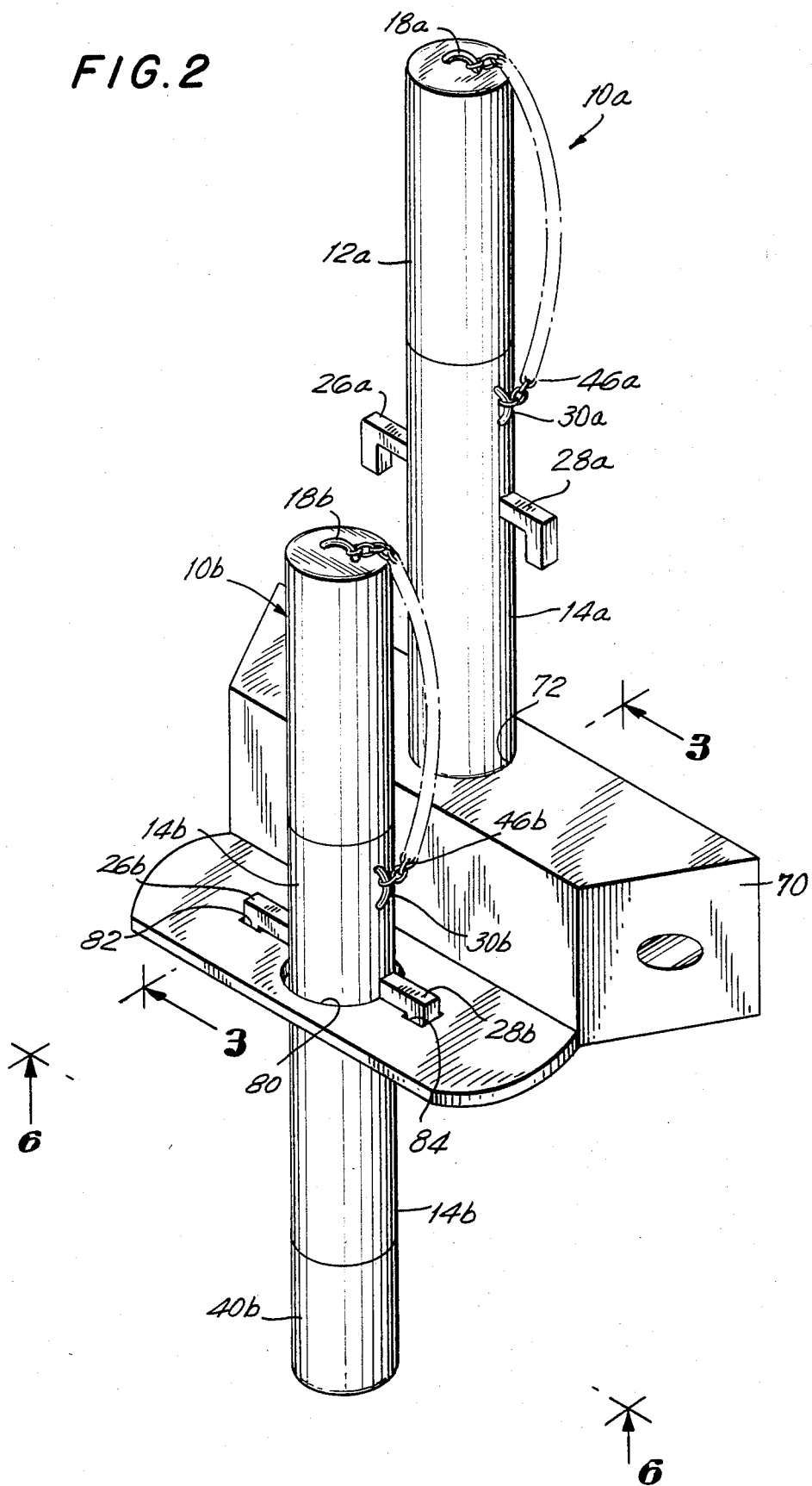
FIG. 2 is a top perspective view of the toothbrush container of FIG. 1 shown in use with a base member manufactured in accordance with the invention.
Figure 3:
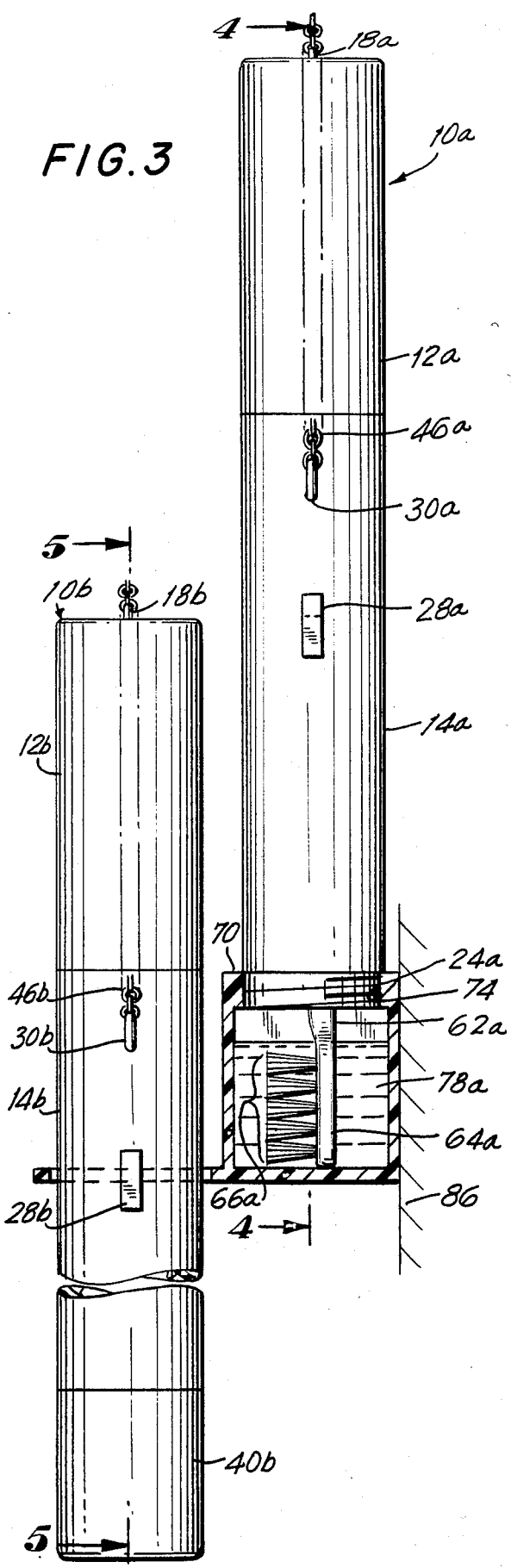
FIG. 3 is a side view of the combination of FIG. 2 shown in partial cross section, taken along the line 3—3 therein.

Preferably, toothbrush container 10 will also include a second bottom member 40 (shown in FIG. 1A), which will have a fifth fastener 42 identical to fourth fastener 32 of first bottom member 16 (such as a third set of threads); and a perforated bottom 44.

Cap 12 may be connected to housing 14 by means of a connector of any conventional type, represented as nylon thread 46, which is connected at one end thereof to first eyelet 18, and at the opposite end thereof to second eyelet 30, connector 46 may alternatively comprise a chain or other known connecting means.

This novel construction of a toothbrush container will enable the user thereof to utilize the device both to allow the toothbrush to dry while it is wet, and also to introduce a disinfectant to the bristles of the brush after use, as will now be explained in greater detail.

When container 10 is in use, a toothbrush 62, having a head 64 with bristles 66 thereon, is disposed between interior shoulders 32, 34 and further disposed so that head 64 and bristles 66 thereof are disposed wholly within first bottom member 16, which preferably contains a disinfectant which may be used to disinfect the bristles 66 after use of toothbrush 62.

After the appropriate disinfection is performed, first bottom member 16 is replaced by second bottom member 40 having perforated bottom 44, thereby allowing bristles 66 to dry by reason of their exposure to the ambient air. Once bristles 66 are dry, first bottom member 16 may be re-secured to housing 14 to protect bristles 66 from contamination. In this fashion, it is possible to provide a convenient toothbrush container which is suitable for transporting the toothbrush and also for providing a suitable environment in which it may be disinfected after use.

FIGS. 2-6 illustrate two toothbrush containers 10a and 10b having identical components differentiated by the notation "a" or "b" appended to the reference numerals, and being utilized together with a base 70 having a first aperture 72 therein, having a sixth fastener 74 which is identical to fourth fastener 24 and fifth fastener 42, in that it is adapted to engage third fastener 22 of housing 14. Aperture 72 leads to a reservoir 76 in which a disinfectant 78 is located.

Base 70 further includes a second aperture 80 having a diameter slightly larger than the exterior of housing 14 of container 10; and two engaging slots 82, 84 which are adapted to receive hooks 26, 28, respectively, of container 10. Additionally, base 70 is preferably adapted to be mounted on a wall 86, for example by means of screws 88 or by other securing means such as adhesive tape (not shown) positioned on the rear thereof.

This configuration of a toothbrush container manufactured in accordance with the invention permits the user thereof to realize the benefits described above.

After brushing his teeth, the user may disinfect toothbrush 62 by placing bristles 66 in disinfectant 78 within reservoir 76 (FIG. 3-6). This is accomplished by inserting toothbrush 62 into aperture 74 and then securing aperture 72 by fastening third and sixth fasteners 24a and 74. In the illustrated embodiment, this requires screwing housing 14 into aperture 72. The presence of housing 14 securely mounted into base 70 maintains toothbrush 62 in the desired position, in contact with disinfectant 78, and also prevents it from becoming accidentally dislodged or contaminated by debris falling through aperture 72 about toothbrush 62.

Once bristles 66 have been disinfected, housing 14 and toothbrush 62 may be disengaged from aperture 72, and second bottom member 40b may be secured to housing 14 by fastening third and fourth fasteners 24b and 42b (FIG. 5). Toothbrush container 10 may then be stored in base 70 by sliding housing 14 through second aperture 80 and engaging hooks 26, 28 thereof with slots 82, 84 (see, e.g. FIGS. 2, 3, 5 and 6).

In this fashion, toothbrush 62 may be disinfected, and then permitted to dry by means of the ambient air. After the bristles have dryed, second bottom member 40 may be replaced by first bottom member 16, and the entire device may be stored in base 70 as described. Thus, by means of the inventive toothbrush container, a toothbrush may be disinfected and then stored conveniently and securely.

In households in which there are a large number of toothbrushes in active use, there may be provided a toothbrush container employing a modified base 90 having a plurality of first apertures 92, second apertures 94, and engaging holes 96, which may be used to house individual toothbrush containers, such as toothbrush container 10' (see FIG. 7).

As will be readily apparent to those skilled in the art, the above description represents a preferred, but nonetheless illustrative, embodiment of the apparatus and operation of the present invention, which invention may be realized in other specific forms without departing from its spirit or essential characteristics. Therefore, the full scope of such invention is to be measured by the appended claims, giving thereto the full range of equivalence which comes within the meaning and range thereof.

I claim:

1. A toothbrush container assembly for holding a toothbrush comprising:
    a base for supporting the assembly, and including first and second apertures, and a slot adjacent said first aperture, therein; and
    a toothbrush container including: a housing having at least one interior shoulder; a cap adapted to engage a first end of said housing; a bottom member adapted to engage a second end of said housing; and securing means, including a hook for engaging said slot, mounted on the exterior of said housing for securing said toothbrush container to said base.

2. The toothbrush container assembly of claim 1, wherein the shoulder is adapted to receive and support the toothbrush while the toothbrush is within the toothbrush container.

3. The toothbrush container assembly of claim 1, wherein the bottom member is perforated.

4. The toothbrush container assembly of claim 1, further comprising:
    a second, imperforate, bottom member.

5. The toothbrush container assembly of claim 1, wherein the second end of the housing includes a first fastener, and the second aperture includes a second fastener adapted to removably engage said first fastener, and thereby retain the housing securely adjacent the second aperture.

6. A toothbrush container assembly for use with a toothbrush and for mounting in a wall comprising:
    a base having a first aperture therein, a slot adjacent said first aperture, an interior reservoir, a second aperture leading from said reservoir to the exterior of said base, said second aperture including a first fastener and means for securing the base to the wall, and
    a toothbrush container assembly having a cap including a second fastener; a central housing including first and second ends, a third fastener disposed at said first end and adapted to removably engage said second fastener, a fourth fastener disposed at said second end of said housing and adapted to removably engage said first fastener; an engaging hook disposed intermediate said first and second ends and adapted to removably engage said slot in said base; an interior shoulder to support the toothbrush while within the container; a first, perforated, bottom member having a fifth fastener adapted to removably engage said fourth fastener; and a second, imperforate, bottom member having a sixth fastener adapted to removably engage said fourth fastener.

7. A toothbrush container assembly for holding a toothbrush comprising:
    a base for supporting the assembly, including: first and second apertures, and an interior reservoir therein, said second aperture leading from the exterior of said base to said interior reservoir; and a toothbrush container including: a housing having at least one interior shoulder; a cap adapted to engage a first end of said housing; a bottom member adapted to engage a second end of said housing; and securing means, mounted on the exterior of said housing for securing said toothbrush container to said base.

* * * * *